US00PP22228P3

(12) United States Plant Patent
Brown et al.

(10) Patent No.: US PP22,228 P3
(45) Date of Patent: Nov. 8, 2011

(54) APPLE TREE NAMED 'NEW YORK 1'

(50) Latin Name: *Malus domestica*
Varietal Denomination: New York 1

(76) Inventors: Susan K. Brown, Geneva, NY (US); Kevin Maloney, Phelps, NY (US)

( * ) Notice: Subject to any disclaimer, the term of this patent is extended or adjusted under 35 U.S.C. 154(b) by 29 days.

(21) Appl. No.: 12/653,569

(22) Filed: Dec. 15, 2009

(65) Prior Publication Data

US 2011/0145956 P1 Jun. 16, 2011

(51) Int. Cl.
*A01H 5/00* (2006.01)

(52) U.S. Cl. ..... Plt./161

(58) Field of Classification Search ..... Plt./161, Plt./172

See application file for complete search history.

*Primary Examiner* — Kent L Bell

(74) *Attorney, Agent, or Firm* — Harris Beach PLLC

(57) ABSTRACT

A new and distinct *Malus domestica* apple tree variety named 'New York 1,' particularly characterized by having attractive red fruits that are sweet, juicy and have a crisp texture and ripen early mid-season. The fruit of 'New York 1' has excellent quality at harvest that it maintains during long storage (100-150 days). Trees are annually productive. 'New York 1' was tested as NY 98804-001.

5 Drawing Sheets

Latin name of the genus and species of the plant claimed: *Malus domestica.*

Variety denomination: 'New York 1'.

BACKGROUND OF THE INVENTION

The present invention relates to a new and distinct variety of apple tree botanically known as *Malus domestica* 'New York 1' and hereinafter referred to by the variety denomination of 'New York 1'.

'New York 1' was selected for its precocious fruiting, attractive fruits and excellent fruit quality at harvest and after cold storage. 'New York 1' fruit are very crisp, juicy and sweet.

The new variety was derived from a controlled pollination in 1998 between the apple variety 'Honeycrisp' (U.S. Plant Pat. No. 7,197) and the apple breeding selection NY 752. NY 752 is a hybrid of 'Starkspur Golden Delicious'×NY 88 ('Monroe'×'Melrose'). One seedling, designated NY 98804-001, was selected from a population of 381 seedlings on the basis of its attractive fruits, precocity and excellent fruit quality. Pollination, cultivation and selection were conducted in Geneva, N.Y. Additional trees of this seedling were produced by clonal propagation in 2002 and subsequent years afterward in Geneva, N.Y.

NY 98804-001 is being named and released as 'New York 1' and is the subject of this invention.

Asexual reproduction at Geneva, N.Y. by budding of the new cultivar 'New York 1' by the inventors shows that the unique combination of characteristics of asexually propagated trees is true to form and transmitted through succeeding propagations.

BRIEF SUMMARY OF THE INVENTION

The following traits of the new variety have been observed and documented in multiple years. The observations and description were collected from test trees grown in Geneva, N.Y. and other test sites within New York State.

The new variety is distinguishable from its parent varieties 'Honeycrisp' and NY 752. Multiple features distinguish the new variety from the parent varieties.

'New York 1' has similar characteristics to 'Honeycrisp' in its sweetness, juiciness and crisp texture, but it is not prone to bitter pit, biennial bearing and other production challenges of 'Honeycrisp' such as susceptibility to soft scald. 'Honeycrisp' leaves have a distinctive leaf mottling disorder that is not seen on 'New York 1'.

When compared to 'New York 1', 'Honeycrisp' fruit have lighter and less uniform fruit color, globose fruit shape, and earlier maturity. NY 752 fruit has later fruit maturity, larger fruit size, less full red color, and a globose fruit shape when compared to 'New York 1'. NY 752 fruits are also prone to fruit russetting.

'New York 1' has smaller average fruit size than either parent and a darker and more uniform red color pattern and more extensive surface color of the fruit.

Fruit of 'New York 1' mature after 'Honeycrisp' and before NY 752. 'New York 1' is unique from either parent in having a conic and uniform fruit shape, sweeter flavor, and longer storage life.

'New York 1' has not been grown and observed in all geographic locations and possible climatic conditions. Slight phenotypic variations might be observed over locations without any change to the genotype.

BRIEF DESCRIPTION OF THE DRAWINGS

The accompanying color photographs illustrate typical specimens of the foliage and fruit and typical anatomical characteristics of the new *Malus* variety 'New York 1', showing the colors as true as is reasonably possible with colored reproductions of this type. Colors in the photographs may differ slightly from the color values cited in the detailed botanical description, which accurately describe the color of 'New York 1'.

View A is a cross-sectional view of 'New York 1' fruit cut longitudinally.

View B is a side view.

View C is a stem-end view.

View D is a bottom or calyx-end view.

View E is a side view.

View F is a cross-sectional view of 'New York 1' fruit cut horizontally.

Figure 1:
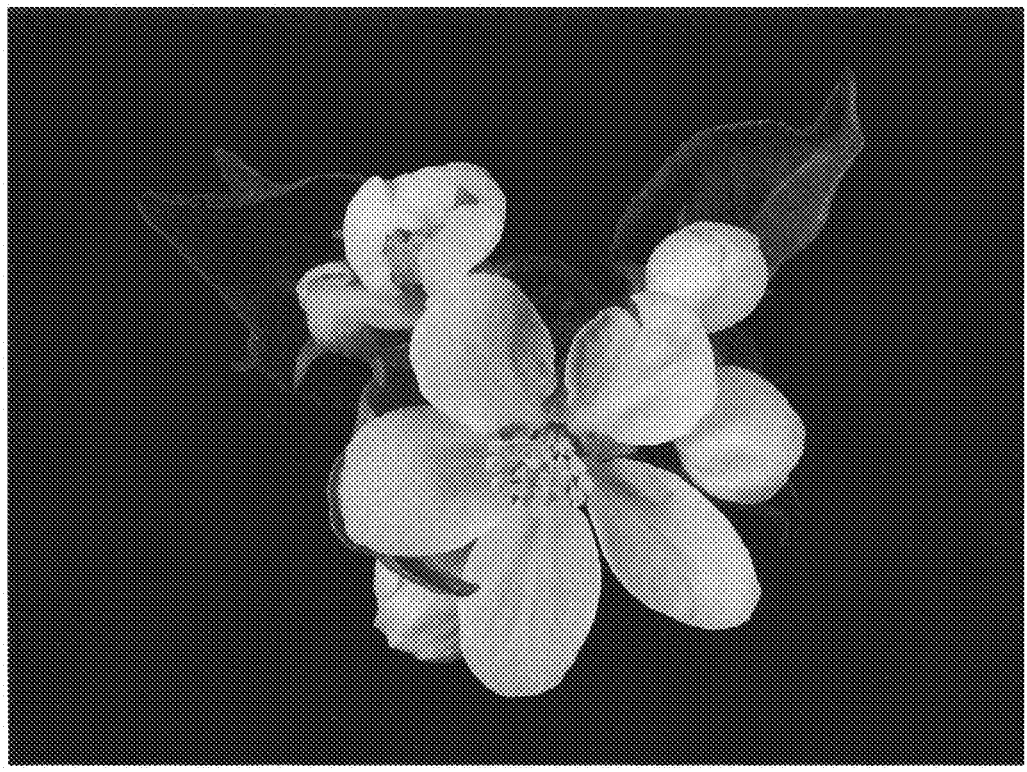
FIG. 1 shows one flower cluster with the primary (dominant) flower open of the 'New York 1'.
Figure 2:
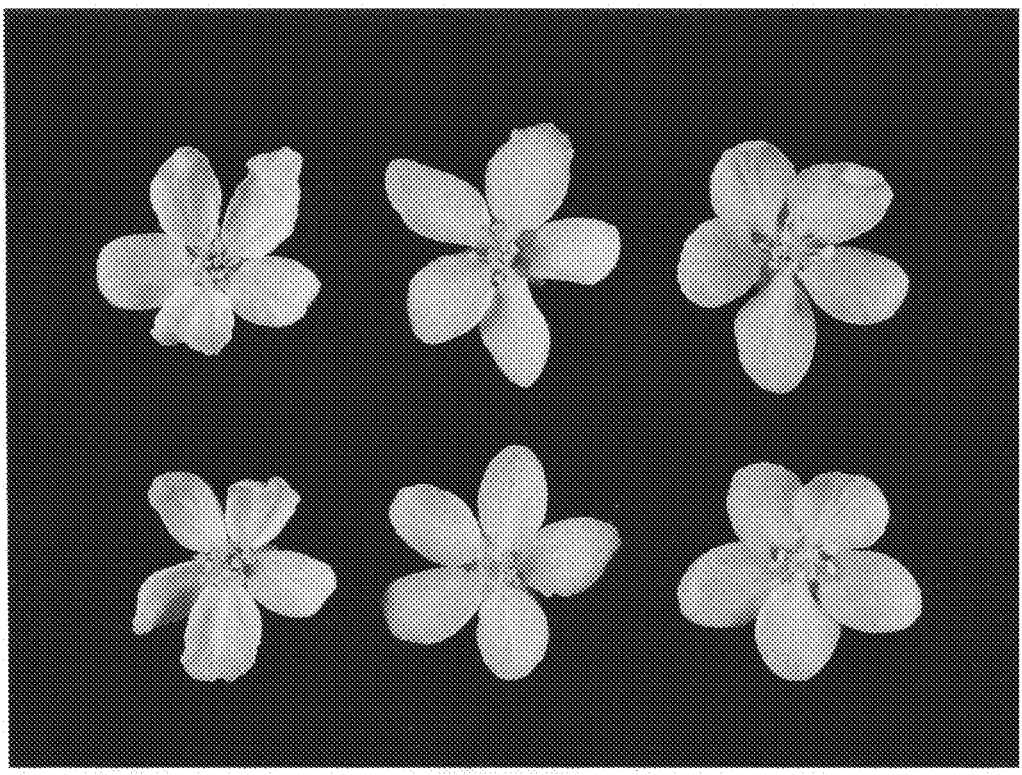
FIG. 2 shows 6 different flowers, two flowers each (from left to right) of the variety 'Honeycrisp' (far left), 'New York 1' (middle) and NY 752 (far right).
Figure 3:
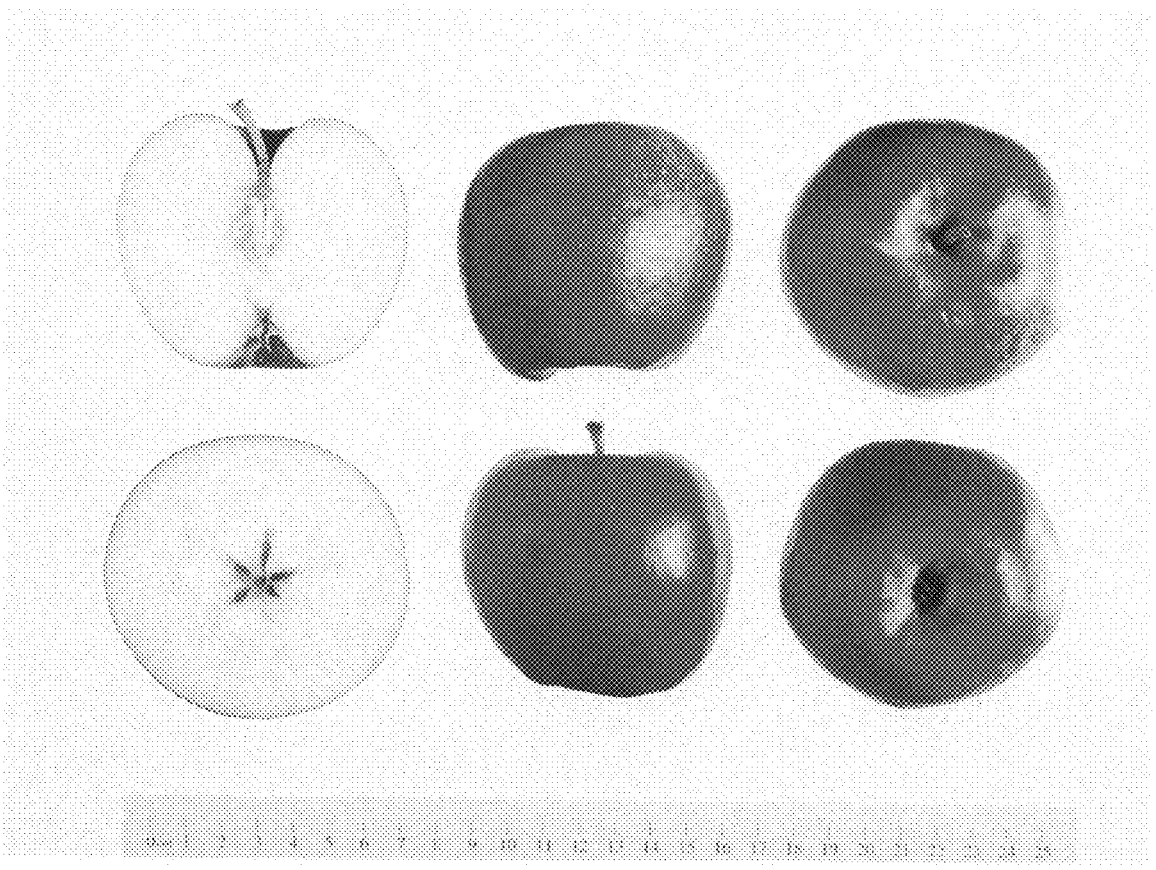
FIG. 3 shows six views of a representative apple of 'New York 1'. From the upper left hand corner and proceeding clockwise.
Figure 4:
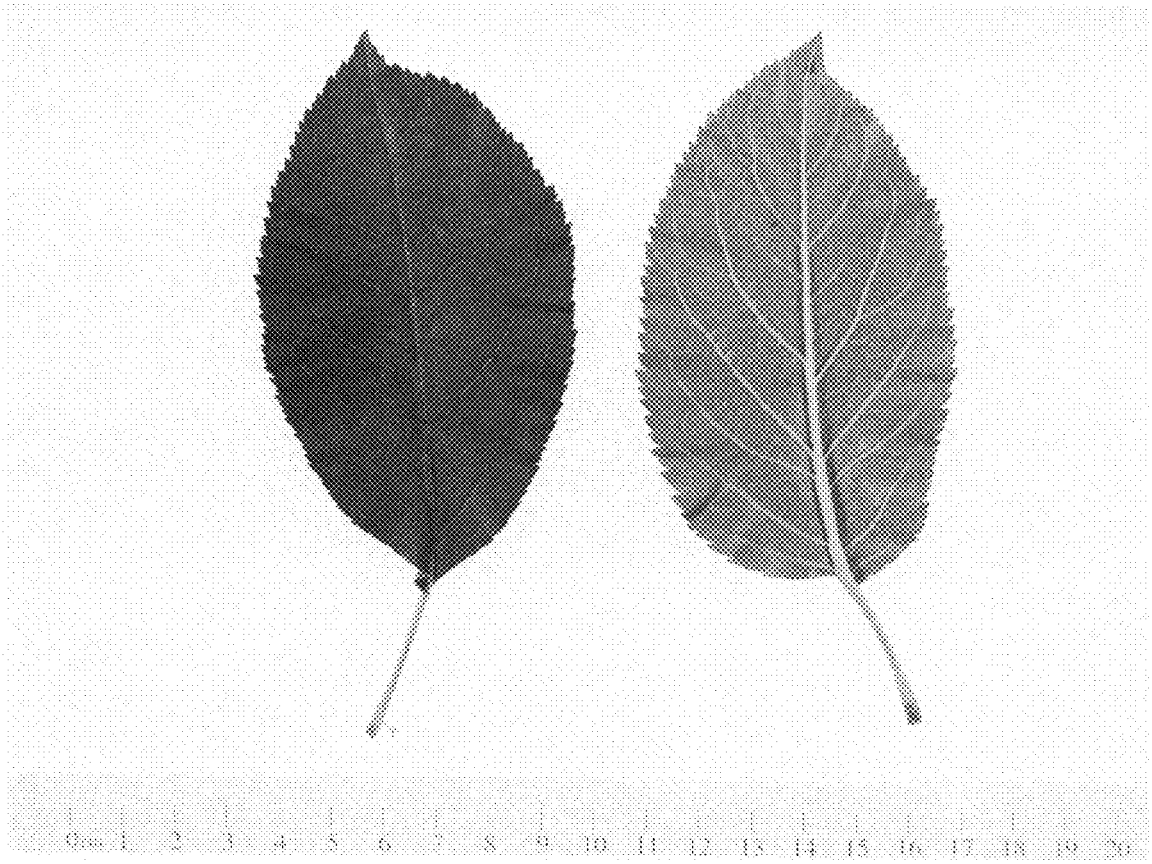

FIG. 4 shows two mature leaves of 'New York 1', one top view and one bottom view of a typical mature leaf.

Figure 5:
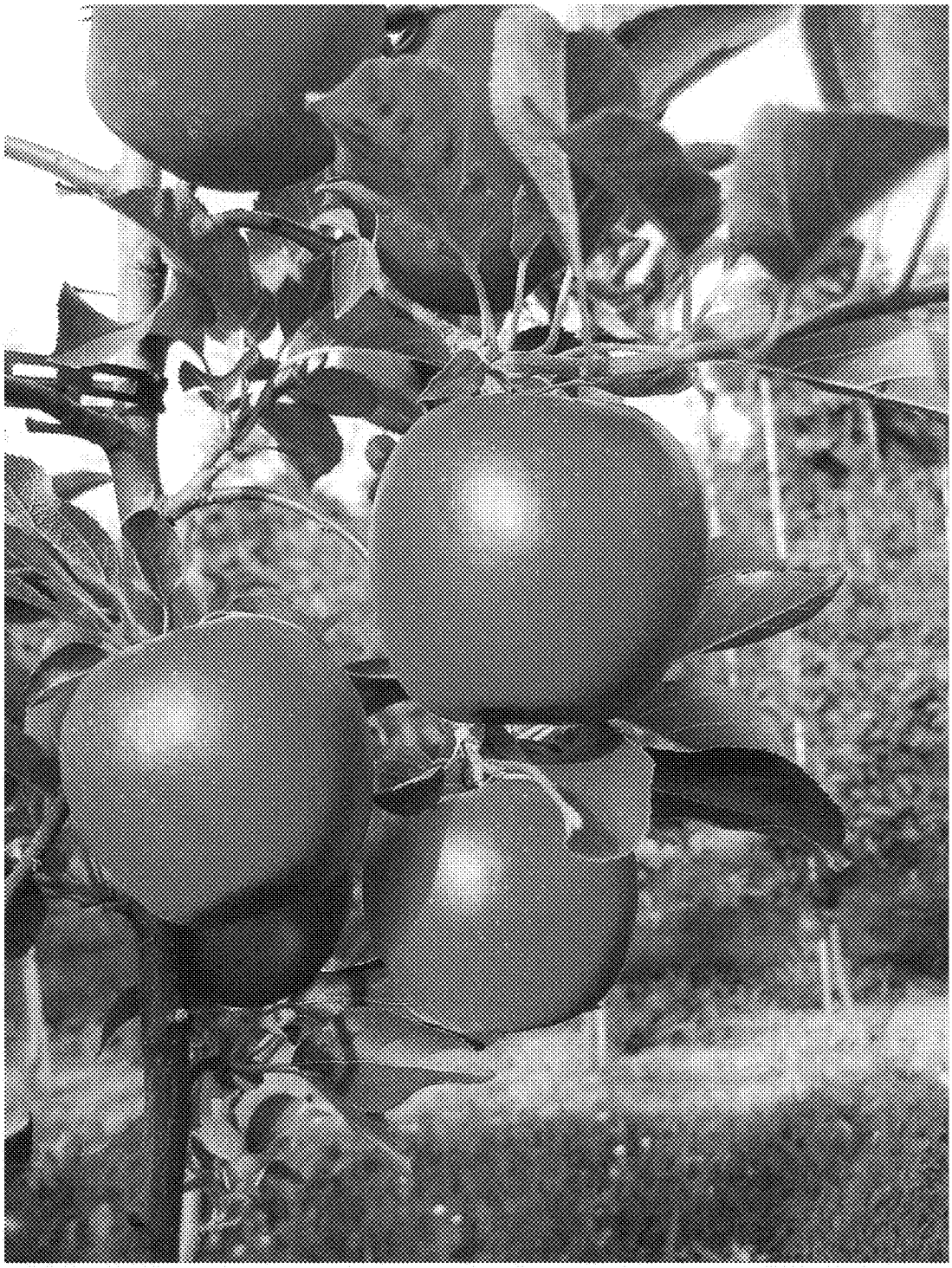

FIG. 5 shows 'New York 1' apples on the tree.

Figure 6:
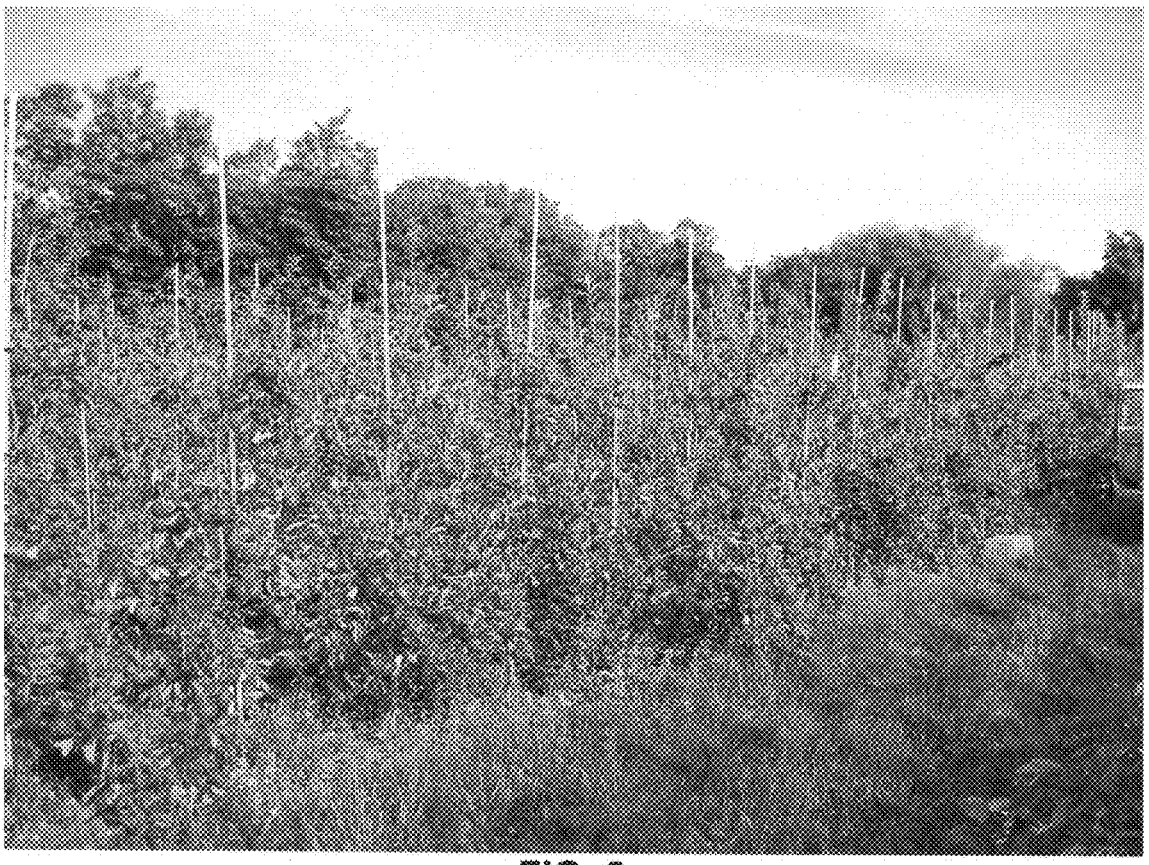

FIG. 6 shows a row of young 'New York 1' trees.

DETAILED BOTANICAL DESCRIPTION

The following is a detailed botanical description of the new variety with color terminology in accordance with The Royal Horticultural Society Colour Chart (R.H.S.C.C.) except where general color terms of ordinary meaning are used as is clear from the context.

The specimens described were grown in Geneva, N.Y. in the United States of America. The observations were made from trees fruiting during 2002 through 2008.

Tree flowering commences on average by May 7th with trees in full bloom by May 12th in Geneva, N.Y. The fruit ripened for eating towards early mid-season. Specifically harvest commences on about September 20th and ends about October 2$^{nd}$ in Geneva, N.Y.

Trees: Small to medium; upright habit; early bearing on spurs; vigor low. Six-year-old trees have an average height of 2.7 m and spread of 1.8 m.

Trunk: Smooth, medium size. Six-year-old trees have an average trunk diameter of 4.2 cm measured at 30 cm above the graft union. Bark is RHSCC Greyed orange 166B. Trunk lenticels average 6 to 8 per square centimeter, RHSCC Greyed-Orange 165B in color, length 2.5 mm to 7 mm, width 1.0 mm to 2.0 mm.

Branches: Moderately thick; smooth; multi-branching; the angle of branching being commonly 45 degrees above the horizontal. Six year old trees have an average of 17 branches per tree, 113 cm in length, 2.3 cm in diameter. Average internode length on a one-year-old shoot is 2.5 cm. Branch color is RHSCC Grey-Brown 199A. Branch lenticles, medium low density average 5 to 7 per square centimeter, RHSCC Grey-Brown 199D in color, length 0.9 mm to 5.5 mm, width 0.5 mm to 1.3 mm. The oldest branches on six-year-old trees have on average 25 spurs per branch, average spur length 55 mm, average spur diameter 5.6 mm, RHSCC Grey-Brown 199A in color.

Leaves: Medium size, ovate in shape with an acute apex and obtuse base, upward pose, concavo-convex in cross section, serrate indentation of margin, medium glossiness of upper sides; medium pubescence on lower side; small to medium stipule size, stipules are free and lateral, spinose shape, 2 mm to 4 mm in length and 0.1 mm to 0.2 mm in width; medium time of bud burst between April 14 to April 18 on average in Geneva, N.Y.

Average leaf blade length 102 mm, blade width 53 mm, petiole length 33 mm, petiole diameter 1.3 mm to 2.0 mm and averages 4.1 serrations per cm of leaf blade margin.

The color of the upper surface of the leaf blade in most similar to RHSCC Green 137A, the bottom surface of the leaf blade is most similar to RHCSS Green 147B, the veins are RHSCC Green 145C and the petioles are RHSCC Green 148D.

Flowers: Medium to late time of beginning of flowering (10% open flowers) on average May 9 to May 12 in Geneva, N.Y.; six flowers per spur, un-open flower bud shape is ovoid, length from base of ovary to tip of flower is 16 mm to 20 mm and 8 mm to 12 mm in diameter, bud color of unopened flower RHSCC Red 54A. Open flowers in cluster overlap, medium size, 47 mm flower diameter and 19 mm height; flat shape; margins of petals barely touching.

Flower petal: Upper surface white RHSCC White 155D, lower surface RHSCC Purple 75C, 5 petals per flower, petal shape oval, margin smooth, apex rounded, base ovate and wide, petal length 21 mm, petal width 14 mm.

Flower pedicel: RHSCC Yellow green 146B, length 19 mm to 23 mm, diameter 1.3 mm to 1.7 mm.

Stamens: 20 stamens per flower, 7-9 mm long, and stamen color RHSCC white 155A. Anther color RHSCC Greyed Yellow 162B.

Style: 7-9 mm long, 5 styles per flower, style color RHSCC Greyed Green 193A, stigma color RHSCC Grey Brown 199C.

Sepals: 5 per flower, upper and lower surface color RHSCC Green 138B, sepal length 8 mm, sepal width 4 mm, apex pointed, deltoid in shape, margin smooth, sepals in reflexed position.

Fruit:

*Fruit.*—Examined at peak maturity.

*Brix.*—15.3°.

*Acidity.*—0.41% malic acid as determined by titration.

*Lbs. Pressure.*—17-19 as measured with a penetrometer.

*Size.*—Medium; axial diameter, 7.3 centimeters, transverse diameter 6.3 centimeters, weight 168 grams.

*Shape.*—Uniform; medium to long conical; symmetrical in side view; medium crowning at distal end.

*Cavity.*—Slightly acuminate. RHSCC Yellow Green 152C and ranging from 152A to 152D. Depth 14.0 mm, Width 24.6 mm.

*Basin.*—Deep, medium breadth; regular and smooth. Depth 14.8 mm, Width 24.4 mm. RHSCC Greyed-Red 180A.

*Stem.*—Medium thickness (2.4 mm) and medium length (17.2 mm). RHSCC Yellow-Green 148C.

*Calyx.*—Persistent, closed, erect.

*Calyx tube.*—Cone shaped.

*Stamen remnants.*—Basal.

*Core lines.*—Meeting (length 32 mm and width 36 mm).

*Core position.*—Median, closed core, small core.

*Carpels.*—Elliptical, inner surface of carpel smooth.

*Skin.*—Medium-thick; 0.17 mm; smooth; bloom of skin, present; cracking tendency of skin, absent; background color, RHSCC greyed-yellow 162B and 160B. Prominent lenticels, round shape, 0.2 mm to 1.1 mm in diameter, 3 to 4 per square cm, RHSCC Greyed-Orange 177B and Greyed-Orange 164D.

*Over-color.*—Approximately ninety percent of over-color of skin; red RHSCC 53B and red 53A, greyed-red180A; mostly solid blush.

*Flesh.*—Juicy; firm (17-19 lbs. at harvest), RHSCC White 155A, rich sweet aroma.

*Texture.*—Crisp and firm.

*Flavor.*—The flavor is sweet and mild with a light acid balance.

*Weight of fruit.*—168 gm.

*Quality.*—Excellent, fresh, juicy and crisp.

*Seeds.*—Five locules (average length 17 mm and width 10 mm), 8 to 10 seeds total. Seed length 8.2 mm.; seed width 4.9 mm.; seed depth 2.6 mm.; acuminate; dried color RHSCC 165A.

*Use.*—Market; dessert, fresh slice, multiple.

*Keeping quality.*—Excellent keeping quality with no disorders after 100 days.

*Resistance to insects.*—Good.

*Resistance to diseases.*—Good.

*Production.*—Early and regular cropping. Very precocious. Fruit yields of 50 to 100 fruits per mature tree have been observed.

*Winter hardiness.*—No winter injury observed on trees grown in USDA plant hardiness zones 4b, 5a, 5b and 6a over several seasons.

*Growth habit.*—Standard habit, fruit borne on short spurs.

*Management.*—Trees require pruning in winter and fruit thinning in early summer. Trees in test plot trained as center leader or slender spindle trees. Natural habit is weak, rounded crown (fruiting leader), with many branches. 'New York 1' has been tested on M.9 (337), 'Pajam 2' and EMLA 9 rootstocks.

What is claimed is:

1. A new and distinct *Malus domestica* apple tree variety named 'New York 1' as described and illustrated herein.

* * * * *